(12) United States Patent
Hahm et al.

(10) Patent No.: US 8,410,046 B2
(45) Date of Patent: Apr. 2, 2013

(54) **ANTIBIOTIC PEPTIDE DERIVED FROM RIBOSOMAL PROTEIN L1 OF *HELICOBACTER PYLORI* AND USE THEREOF**

(75) Inventors: Kyung-Soo Hahm, Seoul (KR); Yoonkyung Park, Jeollanam-do (KR); Seong-Cheol Park, Gwangju (KR); Jong-Kook Lee, Suncheon-si (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 242 days.

(21) Appl. No.: 12/863,406

(22) PCT Filed: Nov. 25, 2008

(86) PCT No.: PCT/KR2008/006938
§ 371 (c)(1),
(2), (4) Date: Nov. 25, 2008

(87) PCT Pub. No.: WO2010/061984
PCT Pub. Date: Jun. 3, 2010

(65) Prior Publication Data
US 2011/0053834 A1     Mar. 3, 2011

(51) Int. Cl.
*A61K 38/00* (2006.01)
*A61K 38/04* (2006.01)
*C07K 7/00* (2006.01)
(52) U.S. Cl. .................................. 514/2.4; 530/326
(58) Field of Classification Search ............. 514/2.4; 530/326
See application file for complete search history.

(56) References Cited

FOREIGN PATENT DOCUMENTS
KR  10-2002-0049443    6/2002
KR  10-2009-0022608  * 3/2009

OTHER PUBLICATIONS

Park et al., Oct. 2, 2007, Amphipathic alpha-helical peptide, HP (2-20), and its analogues derived from *Helicobacter pylori*: Pore formation mechanism in various lipid compositions, Biochimica et Biophysica Acta, 1778: 229-241.*
Tossi et al., 2000, Amphipathic, alpha-Helical Antimicrobial Peptides, Biopolymers, 55: 4-30.*
Zelezetsky et al., 2006, Alpha-helical antimicrobial peptides—Using a sequence template to guide structure-activity relationship studies, Biochimica et Biophysica Acta, 1758: 1436-1449.*
Bevins and Zasloff, "Peptides from Frog Skin," *Annu. Rev. Biochem.*, vol. 59, pp. 395-414, 1990.
Boman, "Antibacterial Peptides: Key Components Needed in Immunity," *Cell*, vol. 65, pp. 205-207, 1991.
Cintas et al., "Enterocins L50A and L50B, Two Novel Bacteriocins from *Enterococcus faecium* L50, Are Related to Staphylococcal Hemolysins," *Journal of Bacteriology*, vol. 180, No. 8, pp. 1988-1994, 1998.
Handwerger and Tomasz, "Antibiotic Tolerance among Clinical Isolates of Bacteria," *Reviews of Infectious Diseases*, vol. 7, No. 3, pp. 368-386, 1985.
Lee et al., "Antifungal Mechanism of an Antimicrobial Peptide, HP (2-20), Derived from N-Terminus of *Helicobacter pylori* Ribosomal Protein L1 against *Candida albicans*," *Biochemical and Biophysical Research Communications*, vol. 291, pp. 1006-1013, 2002.
Lee et al., "Design of novel analogue peptides with potent antibiotic activity based on the antimicrobial peptide, HP (2-20), derived from N-terminus of *Helicobacter pylori* ribosomal protein L1," *Biochimica et Biophysica Acta*, vol. 1598, pp. 185-194, 2002.
Lee et al., "Interactions between the plasma membrane and the antimicrobial peptide HP (2-20) and its analogues derived from *Helicobacter pylori*," *Biochem. J.* vol. 394, pp. 105-114, 2006.
Liu and Tomasz, "Penicillin Tolerance in Multiply Drug-Resistant Natural Isolates of *Streptococcus pneumoniae*," *The Journal of Infectious Diseases*, vol. 152, No. 2, pp. 365-372, 1985.
Miyasaki and Lehrer, "β-sheet antibiotic peptides as potential dental therapeutics," *International Journal of Antimicrobial Agents*, vol. 9, pp. 269-280, 1998.
Ohsaki et al., "Antitumor Activity of Magainin Analogues against Human Lung Cancer Cell Lines," *Cancer Research*, vol. 52, pp. 3534-3538, 1992.
Park et al., "Structure-Activity Relationship of HP (2-20) Analog Peptide: Enhanced Antimicrobial Activity by N-terminal Random Coil Region Deletion," *Biopolymers (Peptide Science)* vol. 88, No. 2, pp. 199-207, 2007.
Park et al., "Amphipathic α-helical peptide, HP (2-20), and its analogues derived from *Helicobacter pylori*: Pore formation mechanism in various lipid compositions," *Biochimica et Biophysica Acta*, vol. 1778, pp. 229-241, 2008.
Pütsep et al., "Antibacterial peptide from *H. pylori*," *Nature*, vol. 398, pp. 671-672, 1999.
Steiner et al., "Sequence and specificity of two antibacterial proteins involved in insect immunity," *Nature*, vol. 292, pp. 246-248, 1981.
Tomasz et al., "Multiple Antibiotic Resistance in a Bacterium with Suppressed Autolytic System," *Nature*, vol. 227, pp. 138-140, 1970.
Tuomanen et al., "Microbiological and Clinical Significance of a New Property of Defective Lysis in Clinical Strains of Pneumococci," *The Journal of Infectious Diseases*, vol. 158, No. 1, pp. 36-43, 1988.

* cited by examiner

*Primary Examiner* — Amber D. Steele
(74) *Attorney, Agent, or Firm* — Klarquist Sparkman, LLP (57) ABSTRACT

The present invention relates to a new antibiotic peptide and a usage thereof, which are derived from ribosomal protein L1, RPL1 of *Helicobacter pylori*. Specifically, the antibiotic peptide comprising the amino acid sequence of SEQ. ID. NO:1 derived from ribosomal protein L1, RPL1 of *Helicobacter pylori* is substituted with a Phenylalanine, which is situated at the first and the eighth position from the antibiotic peptide, or in addition an Asparagine, which is situated at the thirteenth position of the antibiotic peptide, is substituted with lysine, wherein the produced peptides have maintained more decreased cytotoxicity when comparing to the existing antibiotic peptides and can be used as a safe antibiotics by showing more antibacterial activity.

7 Claims, 2 Drawing Sheets

Fig. 1

ANTIBIOTIC PEPTIDE DERIVED FROM RIBOSOMAL PROTEIN L1 OF *HELICOBACTER PYLORI* AND USE THEREOF

CROSS REFERENCE TO RELATED APPLICATION

This is the U.S. National Stage of International Application No. PCT/KR2008/006938 filed Nov. 25, 2008, which was published in English under PCT Article 21(2).

TECHNICAL FIELD

The present invention relates to a novel antibiotic peptide derived from ribosomal protein L1 of *Helicobacter pylori* and use thereof. Specifically, it is related to the antibiotic peptide comprising the amino acid sequence of SEQ. ID. NO:2 produced by substituting a Phenylalanine located at the first and eighth position in the antibiotic peptide comprising the amino acid sequence of SEQ. ID. NO:1, with Alanine, the antibiotic peptide, comprising the amino acid sequence of SEQ. ID. NO: 3, which was produced by substituting Asparagine located at the thirteenth position in the antibiotic peptide with lysine, and the antibiotics containing the antibiotic peptides.

BACKGROUND ART

A bacterial infection is one of the most common and fatal cause to the human diseases, unfortunately, an abuse of the antibiotics has caused an antibiotics resistance to bacterium. In fact, the resistance rate of bacterium to a new antibiotics is much faster than the developing rate of newly made antibiotics analogue. For example, *Enterococcus faecalis, Mycobacterium tuberculosis* and *Pseudomonas aeruginosa*, which can be threaten to a life, have grown the resistance to all antibiotics known up to the present (Stuart B. Levy, *Scientific American*, 46-53, 1998).

The tolerance to the antibiotics is a distinguished phenomenon from the resistance to the antibiotics. The above tolerance to the antibiotics was firstly found from *Pneumococcus* sp in the 1970's and gave an important clue to a mechanism of action of Penicillin (Tomasz et al., *Nature*, 227, 138-140, 1970). The species having the tolerance to the antibiotics stop growing under the normal concentration of the antibiotics, but do not die in the event. The tolerance is caused because an activity of the autolytic enzymes, like autolysin, is not occurred when the antibiotics inhibits a cell wall's synthetase. In case of Penicillin, it may kill a bacterium by activating an endogenous hydrolytic enzymes, but in another case a bacterium may be survived at the time of antibiotics' treating by controlling an activation of the enzyme.

Having the tolerance to a bacterium is clinically very important this is because if it is impossible to kill the tolerance bacterium, the effective of antibiotic's treating to a clinical infection may be decreased (Handwerger and Tomasz, *Rev. Infec. Dis.*, 7, 368-386, 1985). In addition, the tolerance is regarded as a kind of essential prerequisite to generate the bacterium's resistance to the antibiotics as there may be certain survived strain by the antibiotic treating. The survived strain can grow continually under the existence of the antibiotics by way of obtaining a new genetic element having the resistance to the antibiotics. In fact, it is known that all the bacterium having the resistance to the antibiotics also have the tolerance to the antibiotics (Liu and Tomasz, *J. Infect. Dis.*, 152, 365-372, 1985), thus it is necessary to develop the new antibiotics, which can kill a bacterium having the resistant to the antibiotics.

The tolerance can be divided into two cases in a point of a mechanism of action, wherein the first case is a phenotypic tolerance, which is generated from all the bacterium when the growth rate is decreased (Tuomanen E., *Revs. Infect. Dis.*, 3, S279-S291, 1986) and the second case is a genetic tolerance by a mutation, which is generated from a certain bacterium. A basic phenomenon for both cases is the regulation of decreasing the activation of autolysin enzyme. This regulation may be temporary when it is the phenotypic tolerance by an external stimulus, but the regulation may be permanent when it is the genetic tolerance causing the change of channel for regulating a hemolysis. Evidently, the simplest genetic tolerance is the one generated by the lack of autolysin enzyme. However, due to several uncertain reasons, there has been no precedent case of clinically finding the strain having the tolerance by the lack of autolysis enzyme, preferably the tolerance found clinically is made under the process of regulating the activation of autolysin enzyme (Tuomanen et al., *J. infect. Dis.*, 158, 36-43, 1988).

As examined in the above, the development of the new antibiotics is needed in order to kill the bacterium having the resistance to the antibiotics and it is necessary to develop the new antibiotics, which can act independently irrespective of the activation of the autolysin enzyme.

Meanwhile, the bacterium can kill a neighboring bacterium by synthesizing peptides named as a bacteriocin or small organic molecules, wherein those bacteriocins are structurally divided into three kinds. The first kind is lantibiotics, the second kind is nonlantibiotics, and the third kind is the one secreted by a signal peptide (Cintas et al., *J. Bad.*, 180, 1988-1994, 1998). The animal, including the insect, can also produce a peptide antibiotics by themselves (Bevins et al., *Ann. Rev. Biochem.*, 59, 395-414, 1990), wherein there may be three divided groups according to the structure. The first group is a cysteine-rich β-sheet peptide, second group is an α-helical amphiphilic peptide molecule, and third group is a praline-rich peptide (Mayasaki et al., *Int. J. Antimicrob. Agents*, 9, 269-280, 1998). It is well known that these kinds of antibacterial peptides play an important role both in host defense and innate immune system (Boman, H. G., *Cell*, 65:205, 1991; Boman, H. G., *Annu. Rev. Microbiol.*, 13:61, 1995). Additionally, the antibacterial peptides have various structures according to the amino acid sequence. The most common one among the structures is the structure forming an amphiphilic alpha helical structure but without cysteine residue like a cecropin, which is the antibacterial peptide, found in the insect.

Although there has been a hypothesis that a peptic ulcer is caused by a stress and a product of hyperchylia, however interest is on a *Helicobacter pylori* bacterium after it is disclosed that the peptic ulcer is caused by the *Helicobacter pylori* bacterium (Blaser, M J., *Trends Microbiol.*, 1, 255-260, 1991). The *Helicobacter pylori* bacterium belonging to the Gram negative bacterium is very slow in the growth rate and is anaerobic microorganism having a helical body and flagella. RPPL1 protein among the most proteins produced by the *Helicobacter pylori* bacterium is consisted of 230 numbers of amino acid and it is disclosed that the amino terminal of the proteins has the same structure as the cecropin's, especially eight number of amino acid. The RPL1's amino terminal of the *Helicobacter pylori* bacterium has a complete amphiphilic helical-shaped structure (Putsep, K. et al., *Nature*, 398, 671-672, 1999). There has been a report about the mechanism of action that the amphiphilic peptide destructs the lipid of the microorganism by connecting with the lipid of cell membrane of the microorganism or by changing a displacement of the lipid of cell membrane because the amphiphilic peptide is comprised of the structure similar to the lipid of cell membrane. In addition, there has been a report that the amino terminal of RPL1's protein in the *Helicobacter pylori* bacterium also has the antibacterial activity (Putsep K. et al., *Nature*, 398, 671-672, 1999).

Accordingly, a lot of researches have been made, and using these researches, lots of researches to develop the antibiotics to the bacterium have also been tried. The amphiphilic peptides being reported until now are HP (2-20) peptide and melittin peptide and etc.

It has been reported that HP (2-20) peptide, which has the amphiphilic activation among the parts of the amino terminal of RPL1's protein derived from the *Helicobacter pylori* along with having the antibiotic activation, has not a cytotoxicity but has antibacterial activation together with an antifungal effect (*Biochem. Biophys. Res. Commun.*, 2002, 291, 1006-1013, Biochim. Biophys. Acta. 2002, 1598, 185-194).

Besides, it has been reported that the melittin peptide, which occupies more than 50% of the Pan-Cake among the bee venom's ingredients, wherein a carboxy terminal has become amidation. And it has been reported that the melittin peptide can destruct the cell of the higher animal well under the low concentration due to having the high cytotoxicity to a eukaryotic cell and has the antibacterial activation to the Gram negative bacterium and Gram positive bacterium (Habermann, E., *Science*, 177: 314, 1972; Steiner, H., et al., *Nature*, 292: 246, 1981; Tosteson, M. T., et al., *Biochemistry*, 228: 337, 1987).

What is more, the amphiphilic peptide belonging to the cecropin series HP (2-20) comprising the amino acid similar to the HP (2-20) was firstly found from a *drosophila*, and since then it is also found from a silk worm pupa and a small intestine of a pig. Among them, it has been reported that a cecropin A has the high antibacterial activation, but has the low antifungal and anticancer effect (Boman, H. G. and Hultmark, D., *Annu. Rev. Microbiol.*, 41: 103, 1987).

Also, in addition to the research about the activation of the above amphiphilic peptide, it is confirmed that the characteristic of sequence is closely related to the antibacterial activation when inspecting the amino acid sequence and protein structure of the amphiphilic peptide. Therefore, a conjugation peptide can be made by substituting the certain parts of the sequence with the similar amino acid using the amino acid sequence of the above amphiphilic peptide or by recombinating the certain sequences. And the production of a new synthetic peptide having the excellent antibacterial, antifungal or anticancer activation can be also made by inversing the certain parts of the function of the peptide sequence (Chan, H. C., et al., *FEBS Lett.*, 259: 103, 1989; Wade, D., et al., *Int. J. Pept. Prot. Res.*, 40: 429, 1992).

In fact, a synthetic peptide mag A and mag G, which have the anticancer effect, were prepared by applying the amphiphilic peptide and the potency was also reported (Ohsaki, et al., *Cancer Res.*, 52: 3534, 1992). Additionally, the synthetic peptides having the antifungal activation by mutually connecting the amino acids in the amphiphilic parts, flexibility parts and hydrophobic parts from a magainin 2 and melitin peptides have been developed, and those developed peptides was granted as a patent because of the action to bacteria and the strain in a fungus (KR Patent no. 0204501). Also, the inventors for the present invention substituted the certain amino acids of the existing HP (2-20) peptide with a tryptophan and resulted in the addition of hydrophobic (sequence no. 2) By doing so, the inventors confirmed the addition of the antibiotics effect and the present invention was granted a patent with the antibiotics peptide (KR Patent no. 0459808). Also, the present inventors synthesized the antibiotics peptide, which was only left the helical structure of the peptide but added the cation property, by amputating the relaxation structure from the antibiotic peptide comprising of the helical structure in a straight line, wherein they confirmed the high effect of the antibacterial and antifungal of the above peptide without having the cell toxicity and filed an application with the above contents (KR Patent no. 10-2007-0088127).

Recently, lots of researches to develop an excellent antibiotic peptide having more antibacterial activity and less cell toxicity than the existing antibiotic peptides.

Accordingly, the present inventors have tried to develop the excellent antibiotic peptide using the existing antibiotic peptide. By the process of development try, they have completed the present invention by confirming the fact that both the new peptide comprising of amino acid sequence of SEQ. ID. NO:2, which was produced by substituting both the first and the eighth position of Phenylalanine from the antibiotic peptide each alanine comprising the amino acid sequence of the existing SEQ. ID. NO:1, and the new peptide comprising the amino acid sequence of SEQ. ID. NO:3, which was produced by substituting Asparagine at the thirteenth position of the above peptide with lysine have less cell toxicity and have similar antibacterial activity or more antibacterial activity than the antibiotic peptide comprising of amino acid sequence of SEQ. ID. NO: 1

DISCLOSURE

The Sequence Listing is submitted as an ASCII text file in the form of the file named Sequence_Listing.txt, which was created on Jun. 28, 2010, and is 1173 bytes, which is incorporated by reference herein.

TECHNICAL PROBLEM

It is an object of the present invention to provide the new antibiotic peptide having excellent antibacterial activity and no cytotoxicity, and the antibiotics and food complement comprising the new peptide.

TECHNICAL SOLUTION

To achieve the above object, the present invention provides an antibiotic peptide comprising the amino acid sequence of SEQ. ID. NO: 1, wherein Phenylalanine, which is situated at the first and the eighth position of the antibiotic peptide, is substituted with alanine and cytotoxicity is decreased.

The present invention also provides the antibiotic peptide having decreased cytotoxicity comprising the amino acid sequence of SEQ. ID. NO: 2, wherein an Asparagine, which is situated at the thirteenth position of the antibiotic peptide, is substituted with a positive charge amino acid.

The present invention further provides an antibiotics comprising the antibiotic peptide as an active ingredient.

The present invention also provides a method for the prevention or treatment of the pathogenic bacterial disease containing the step of administering a pharmaceutically effective dose of the antibiotics of claim 7 to a subject.

The present invention also provides a use of the antibiotic peptide of claim 1 or claim 3 for the antibiotics.

The present invention also provides a food complement or a food addition agent containing the antibiotic peptide.

In addition, the present invention provides a use of the antibiotic peptide for the food complement or the food addition agent.

Hereinafter, the present invention is described in detail.

The present invention also provides the antibiotic peptide having decreased cytotoxicity comprising the amino acid sequence of SEQ. ID. NO:2, wherein an Asparagine, which is situated at the thirteenth position of the antibiotic peptide, is substituted with a positive charge amino acid. The antibiotic peptide is preferred to having the amino acid sequence of SEQ. ID. NO: 2, but not always limited thereto.

The peptide of the present invention can be prepared by the peptide synthetic method known in the art, but the method of production is not always limited thereto.

The antibiotic peptide in the present invention was prepared by substituting Phenylalanine at the first and eighth position of the amino acid sequence of HPA3NT3 peptide, which was produced by the KR application number 10-2007-0088127.

In a helical wheel diagram of HPA3NT which is a maternal peptide comprising the amino acid sequence of SEQ. ID. NO: 1, wherein two Phenylalanines exist in a line at the first and eight position of the hydrophobic parts. In case that two Phenylalanins exist in a line, the cytotoxicity is generated from the normal cell. Thus, NT3-F1AF8A comprising the amino acid sequence of SEQ. ID. NO:2 has been designed by substituting the two Phenylalanines existed in a line with Alanine (See Table 1).

The antibiotic peptide has prominently decreased the cytotoxicity when comparing to the existing HPA3NT3 and the antibacterial activity has slightly decreased in some of the strains, but it was not a significant limit. Therefore, the main feature of the present invention is that the antibiotic peptide maintains prominently less cytotoxicity than the HPA3NT3's of the maternal peptide and has similar antibacterial activity.

The feature of the antibiotic peptide of the present invention is to have the antibacterial activity to the Gram negative bacterium and/or Gram positive bacterium The Gram negative bacterium is preferably more than one which is selected from the group comprising of *Escherichia coli, Pseudomonas aeruginosa, Proteus vulgaris* and *Salmonella typhimurium*, and the Gram positive bacterium is preferably more than one which is selected from the group comprising of *Staphylococcus aureus, Listeria monocytogenes, Staphylococcus epidermidis, Bacillus subtilis*, but not always limited thereto.

The present inventors measured a Minimal Inhibitory Concentration; hereinafter referred to as MIC, to a various kinds of bacteria in order to confirm whether NT3-F1AF8A of the antibiotic peptide has the antibacterial activity. As a result, it is confirmed that the antibiotic peptide (NT3-F1AF8A) has similar or decreased antibacterial activity on the some strains when comparing to the maternal peptide (HPA3NT3), but the above decreased limit was not the significant limit in showing the effect of the antibacterial activity. Therefore, it shows that the peptide of the present invention has similar antibacterial effect in comparison with the existing antibiotic peptide (See Table 2).

The antibiotic peptide of the present invention features that there are little cytotoxicity.

The present inventors measured a hemolytic activity of erythrocyte to the antibiotic peptide using normal person's blood in order to check the cytotoxicity of the above antibiotic peptide (NT3-F1AF8A). As a result, the antibiotic peptide (NT3-F1AF8A) of the present invention did not generate hemolytic phenomenon by the concentration of 200 μM, on the contrary the maternal peptide did generate 37.23% of hemolytic phenomenon under the same concentration. Therefore, it is confirmed that the antibiotic peptide of the present invention has little cytotoxicity (See Table 3)

Figure 1:
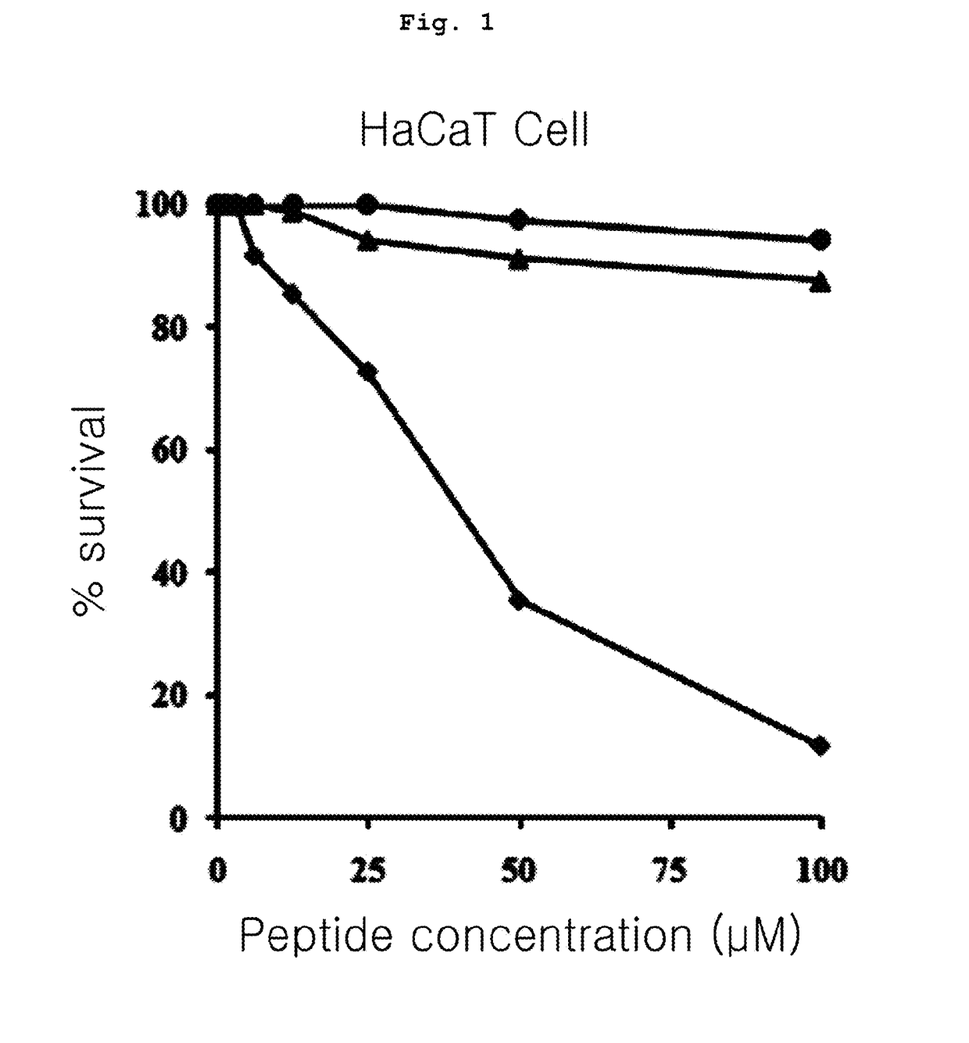
FIG. 1 is a diagram illustrating the cytotoxicity of the antibiotic peptides (control group 1, control group 2 and experimental group) of the present invention in HaCaT cell line:
●: The antibiotic peptide comprising the amino acid sequence of Sequence No. 3, ▲: The antibiotic peptide comprising the amino acid sequence of Sequence no. 2, ◆: The antibiotic peptide comprising the amino acid sequence Sequence No. 1.
Figure 2:
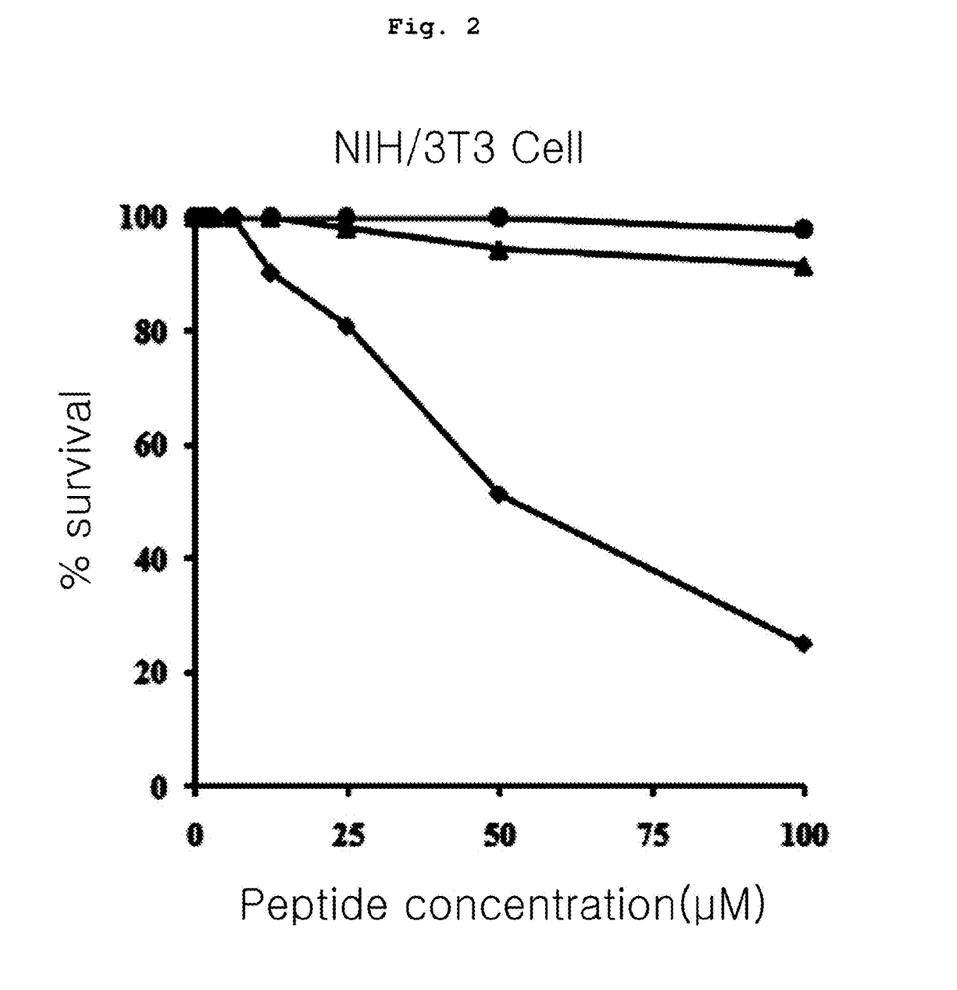
FIG. 2 is a diagram illustrating the cytotoxicity of the antibiotic peptides (control group 1, control group 2 and experimental group) of the present invention in NIH3T3 cell line:
●: The antibiotic peptide comprising the amino acid sequence of Sequence No. 3, ▲: The antibiotic peptide comprising the amino acid sequence of Sequence no. 2, ◆: The antibiotic peptide comprising the amino acid sequence of Sequence No. 1.

The present invention investigated the cell viability after administering the antibiotic peptide to HaCaT cell line and NIH3T3 cell line respectively in order to investigate the cytotoxicity from a normal cell line of NT3-F1AF8A, which is the antibiotic peptide of the present invention. As a result, it is confirmed that the antibiotic peptide (NT3-F1AF8A) of the present invention showed little cytotoxicity from the above two cell lines, but the maternal peptide (HPA3NT3) showed high cytotoxicity. Thus, it is confirmed that the antibiotic peptide of the present invention has little cytotoxicity from the normal cell line (See Drawing 1 and Drawing 2).

The present invention also provides the antibiotic peptide having decreased cytotoxicity and increased antimicrobial activity comprising the amino acid sequence of SEQ. ID. NO:2, wherein an Asparagine, which is situated at the thirteenth position of the antibiotic peptide, is substituted with a positive charge amino acid.

The positive charge amino acid is preferably the one selected from the group comprising of lysine, arginine and histidine and more preferably lysine, but not always limited thereto.

It is preferably for the antibiotic peptide to be comprised of the amino acid sequence of SEQ. ID. NO:3, but not always limited thereto.

The peptide of the present invention can be produced by the peptide synthetic method known in the art, but the method of production is not always limited thereto.

In the HPA3NT3 of maternal peptide comprising the amino acid sequence of SEQ. ID. NO: 1, the present inventors have designed NT3-F1AF8A comprising the amino acid sequence of SEQ. ID. NO:2 by substituting two Phenylalanine existed in a line with alanine excluding phenyl, wherein the cytotoxicity was prominently decreased from some strains comparing to HPA3NT3 and the bacterial activity was also decreased in the other strains. Therefore, the present invention has designed NT3-F1AF8A-A2 peptide comprising the amino acid sequence of SEQ. ID. NO:3 by substituting Asparagine situating at the thirteenth position of negative charge amino acid with lysine of positive charge amino acid in order to increase the positive ion charge of the NT3-F1AF8A peptide. As a result, it is confirmed that the cytotoxicity was maintained prominently low than the maternal peptide of HPA3NT3's, but the antibacterial activity was enhanced better than the maternal peptide of HPA3NT3's (See Table 1).

The feature of the antibiotic peptide of the present invention is to have the antibacterial activity to the Gram negative bacterium and/or Gram positive bacterium The Gram negative bacterium is preferably more than one which is selected from the group comprising of *Escherichia coli, Pseudomonas aeruginosa, Proteus vulgaris* and *Salmonella typhimurium*, and the Gram positive bacterium is preferably more than one which is selected from the group comprising of *Staphylococcus aureus, Listeria monocytogenes, Staphylococcus epidermidis, Bacillus subtilis*, but not always limited thereto.

The present inventors measured a Minimal Inhibitory Concentration; hereinafter referred to as MIC, to a various kinds of bacteria in order to confirm whether NT3-F1AF8A-A2 of the above antibiotic peptide has the antibacterial activity. As a result, it is confirmed that the antibiotic peptide (NT3-F1AF8A-A2) has similar or more than 2 times of antibacterial activity when comparing to the maternal peptide (HPA3NT3) and NT3-F1AF8A. Therefore, it shows that the peptide of the present invention has the prominent antibacterial effect in comparison with the existing antibiotic peptide (See Table 2).

The antibiotic peptide of the present invention features that there are little cytotoxicity.

The present inventors measured a hemolytic activity of erythrocyte to the antibiotic peptide using ordinary person's blood in order to check the cytotoxicity of the above antibiotic peptide (NT3-F1AF8A). As a result, the antibiotic peptide (NT3-F1AF8A) of the present invention did not generate hemolytic phenomenon by the concentration of 200 µM, on the contrary the maternal peptide did generate 37.23% of hemolytic phenomenon under the same concentration. Therefore, it is confirmed that the antibiotic peptide of the present invention has little cytotoxicity (See Table 3)

The present inventors investigated the cell viability after administering the antibiotic peptide to HaCaT cell line and NIH3T3 cell line respectively in order to investigate the cytotoxicity from a normal cell line of NT3-F1AF8A-A2, which is the antibiotic peptide of the present invention. As a result, it is confirmed that the antibiotic peptide (NT3-F1AF8A-A2) of the present invention showed little cytotoxicity from the above two cell lines, but the maternal peptide (HPA3NT3) showed high cytotoxicity. Thus, it is confirmed that the antibiotic peptide of the present invention has little cytotoxicity from the normal cell line (See Drawing 1 and Drawing 2).

In addition, the present invention provides the antibiotic peptide with maintaining alanine at the first and eighth position of the amino acid sequence comprising the above SEQ. ID. NO:2 and having more than 90% of homology of the sequence.

In the synthetic peptide comprising the amino acid sequence of SEQ. ID. NO: 2 of the present invention, wherein the synthetic peptide can include the antibacterial peptide after substitutin each amino acid with the amino acid having the similar structure, or substitutin amino group of the amino terminal or carboxyl group of the carboxy terminal with another functional group.

In addition, the present invention provides the antibiotic peptide with maintaining alanine at the first and eighth position of the amino acid sequence comprising the above SEQ. ID. NO:3 and lysine at the thirteenth position, and having more than 90 percentage of homology of the above sequence.

In the synthetic peptide comprising the amino acid sequence of SEQ. ID. NO:3 of the present invention, wherein the synthetic peptide can include the antibacterial peptide after substituting each amino acid with the amino acid having the similar structure, or substituting amino group of the amino terminal or carboxyl group of the carboxy terminal with another functional group.

The present invention further provides the antibiotics having more than one of the antibiotic peptides of the present invention as an active ingredient.

The antibiotic peptide comprising the amino acid sequence of the above SEQ. ID. NO: 2, the antibiotic peptide comprising the amino acid sequence of the above SEQ. ID. NO: 3, and its derivatives have a similar or the higher antibacterial activity on the various bacteria strains than the existing antibiotic peptide, and they can be used as the active ingredient of the antibiotics as it has little cytotoxicity under the high concentration.

It is preferably for the antibiotics to include the antibiotic peptide comprising the amino acid of the above SEQ. ID. NO:2, the amino acid of the above SEQ. ID. NO:3, or the peptide having more than 90% of homology of the above sequence, but not always limited thereto.

The above antibiotics features that it has the antibacterial activity on the Gram negative bacterium and/or Gram positive bacterium.

The Gram negative bacterium is preferably more than one which is selected from the group comprising of *Escherichia coli, Pseudomonas aeruginosa, Proteus vulgaris* and *Salmonella typhimurium*, and the Gram positive bacterium is preferably more than one which is selected from the group comprising of *Staphylococcus aureus, Listeria monocytogenes, Staphylococcus epidermidis, Bacillus subtilis*, but not always limited thereto.

The antibiotics of the present invention can be administered parenterally and be used in general forms of pharmaceutical formulation.

When the antibiotics of the present invention is used as the pharmaceutical formulation, it can additionally include more than one of the same or similar function of active ingredient.

In other words, it can be in fact administered in a various formulation, and can be pharmaceutically prepared by using generally used diluents or excipients such as fillers, extenders, binders, wetting agents, disintegrating agents and surfactant. Formulations for parenteral administration are sterilized solutions, water insoluble excipients, suspensions, emulsions, lyophilized preparations and, suppositories. As an insoluble excipients and suspensions, Propylene glycol, Polyethylene glycol, vegetable oil like olive oil, injectable ester like ethyloleate, etc can be used. Suppositories can contain witepsol, macrogo, tween 61, cacao butter, laurin butter, glycerogelatin, etc.

Also, the antibiotic peptide of the present invention can be used by mixing with the carrier, which are allowed as an agent, like physiological salt solution or organic solvent and in addition carbohydrate like Glucose, sucrose or Dextran, antioxidants like ascorbic acid or Glutathione, chelating agents, low molecular protein or stabilizers Glucose, sucrose or Dextran can be used as an agent.

The present invention also provides a method for the treatment of pathogenic bacterial disease, including the steps administering the antibiotics on a subject with a pharmaceutically effective dose.

The present invention also provides a method for the prevention of pathogenic bacterial disease, including the steps administering the antibiotics on a subject with a pharmaceutically effective dose.

The antibiotic of the present invention can be administered parenterally and be used in general forms of pharmaceutical formulation.

The dosage of the antibiotics is 0.001~10 mg/kg based on the antibiotic peptide amount, more preferably 0.01~1 mg/kg, and administration frequency is preferably 1-3 times a day.

The effective dosage of the antibiotics can be administered to a patient with a single dose in a bolus type or by way of infusion for a very short time, but fractionated treatment protocol, which is administered with a multiple for a long time, can be accepted.

The effective dosage of the antibiotics can be determined according to administration method and administration frequency, age and health condition, etc. Therefore, considering the point, a person with skill in the art can determine the effective dosage for a certain purpose as a pharmaceutical composition of the peptide.

The present invention also provides a use of the production of the antibiotics with the antibiotic peptide of the present invention.

The synthetic peptide comprising the amino acid sequence of the SEQ. ID. NO: 3 and its derivatives have more radical antimicrobial activity on the various bacteria strains than the existing antibiotic peptide, and it can be used as the active ingredient as there is little cytotoxicity under the high concentration.

The present invention also provides a food complement or a food addition agent containing the antibiotic peptide of claim 3 or claim 3.

In addition, the present invention provides a use of the antibiotic peptide of claim 1 or claim 3 for the food complement or the food addition agent.

The antibiotic peptide of the present invention can be used as a food additive. In that case, the antibiotic peptide can be added as it is or used with other food complements according to the conventional method. The mixing ratio of active ingredients can be regulated according to the purpose of use. In general, the antibiotic peptide is added by up to weight part and preferably by up to 10 weight part. However, if long term administration is required, the content can be lower than the above but higher content can be accepted as well since the antibiotic peptide has been proved to be very safe.

The food herein is not limited. For example, the antibiotic peptide can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the health food can be included.

ADVANTAGEOUS EFFECT

The antibiotic peptide of the present invention has more radical antimicrobial activity both on Gram positive bacterium and Gram negative bacterium than the existing antibiotic peptide, but has no cytotoxicity so that it can be used as a safe antibiotics to a human.

DESCRIPTION OF DRAWINGS

The application of the preferred embodiments of the present invention is best understood with reference to the accompanying drawings, wherein.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Experimental Example 1

Synthesis and Isolate Refinement of the Antibiotic Peptides

The present inventors, according to the liquid-solid method (Merrifield, R B., *J. Am. Chem. Soc.*, 85, 2149, 1963), substituted two phenylalanines, which is situated at the first and the eighth position in HPA3NT3 (control group) comprising the amino acid sequence of SEQ. ID. NO:1, maternal peptide, with alanine not including phenyl group, and synthesized NT3-F1AF8A peptide (Sequence no. 2)(experimental group 1), wherein in order to increase positive ion charge from the NT3-F1AF8A peptide they substituted asparagine, which is situated at thirteenth position in HPA3NT3 and negative charge amino acid, with lysine, which is positive charge amino acid, and synthesized NT3-F1AF8A-A2 peptide (Sequence no. 3) (experimental group 2) (Table 1).

Specifically, a peptide having —NH2 form at the carboxyl terminal prepared by the present invention used Rink Amide MBHA-Resin as a stating substance and a peptide having —OH form at the carboxyl terminal used Fmoc-amino acid-Wang Resin as a starting substance. An extension of peptide chain by Fmoc-amino acid coupling was prepared by the DCC (N-hydroxybenzo triazole (HOBt)-dicyclo-hexycarbodiimide) method. The present inventors removed Fmoc group with NMP (20% piperidine/N-methylpyrolidone), which was followed after coupling Fmoc-amino acid in the amino acid terminal of each peptide. And then, they washed the Fmoc-amino acid out several times with NMP and DCM (dichloromethane), and dried to nitrogen gas. And the present inventors removed tutamina and isolated peptide from resin after treating TFA (trifluoroacetic acid)-phenol-thioanisole-$H_2O$-triisopropylsilane (85:5:5:2.5:2.5, vol./vol.) solution for about 2-3 hours, and precipitated peptide using diethylether. They refined the crude peptide using reverse phase (RP)-HPLC column (Delta Pak, $C_{18}$ 300, 15, 19.0 mm×30 cm, Waters, USA) from the acetonitrile gradient including 0.05% TFA. The present inventors decompressively concentrated the residue after hydrolyzing a synthetic peptide into 6 N HCl at 110, and measured the composition of amino acid by amino acid analyzer (Hitachi 8500 A) after making it unfreezed in 0.02 N HCl. After checking purity of the composition of the peptides by that way, it was confirmed to have more than 95% in the purity. Also, after comparing it with the molecular weight, which was obtained by calculating molecular weight from the amino acid sequence using MALDI mass spectrometry (Hill, et al., *Rapid Commun. Mass Spectrometry*, 5: 395, 1991), it was confirmed that the value is identical with the molecular weight, which was obtained by calculating molecular weight from the amino acid sequence using MALDI mass spectrometry.

TABLE 1

| Amino acid sequence of the peptide | | |
|---|---|---|
| Peptide | Amino acid sequence | Net charge |
| HPA3NT3 | FKRLKKLFKKIWNWK-NH2 (Sequence no. 1) | +7 |
| NT3-F1AF8A | AKRLKKLAKKIWNWK-NH2 (Sequence no. 2) | +7 |
| NT3-F1AF8A-A2 | AKRLKKLAKKIWKWK-NH2 (Sequence no. 3) | +8 |

Experimental Example 2

Measurement of Antimicrobial Activity

The present inventors measured MIC, which is the minimum concentration of not divided bacterial cell, in order to compare the antimicrobial activity of the peptide prepared by the method of <experimental example 1>.

More specifically, the present inventors used *Escherichia coli, Pseudomonas aeruginosa, Proteus vulgaris, Salmonella typhimurium* as a Gram negative bacterium and used *Staphylococcus aureus, Listeria monocytogenes, Staphylococcus epidermidis, Bacillus subtilis* as a Gram positive bacterium. In addition, *Escherichia coli* (ATCC 25922), *Listeria monocytogenes* (ATCC 19115), and *Staphylococcus aureus* (ATCC 25923) were provided by "American Type Culture Collection" and *Bacillus subtilis* (KCTC 1918), *Streptococcus epidermidis* (KCTC 3096), *Pseudomonas aeruginosa* (KCTC 1637) and *Proteus vulgaris* (KCTC 2433) were provided by "Korean Collection for Type Cultures". After culturing each strain by up to mid-log phase in LB medium (1% Bacto tryptone, 0.5% extraction of Bacto yeast, 1% sodium chloride; Sigma, USA) and diluting it by the bacterial cell concentration of $1 \times 10^4$ cell/100 μl with 1% Bacto pepton medium (Difco, USA), they inoculated the strain to Microtitrate Plate (Nunc, USA). The present inventors added both the peptide of the present invention (experimental group 1 and 2) synthesized in the <experimental example 1> and maternal peptide(control group) into the plate after diluting separately by 1/2 times from 25 μM/well, and cultured them for 6 hours at 37° C. In addition, they measured absorbance under 620 nm of wavelength using Microtitrate Plate reader (Merck Elisa reader, Germany) and determined the MIC value of each strain, after then they described the final result in the following Table 2.

Therefore, it is confirmed that both the Gram positive bacterium and Gram negative bacterium have similar or more antimicrobial activity to the existing antibiotic peptide (Table 2).

Experimental Example 3

Measurement of Hemolytic Activity

The present inventors measured erythrocyte hemolytic activity of the peptides in order to compare the cytotoxicity of the peptides prepared by the method of the <experimental example 1>.

Firstly, the present inventors diluted human erythrocyte with phosphate buffer (PBS, pH 7.0) to be a 8% concentration and then, they diluted each described peptide comprising the amino acid sequence of SEQ. ID. NO: 1 to 3 in the Table 1 continually at the 1/2 concentration starting from 200 μM and make them reacted for 1 hour at 37. After then, the present inventors measured the amount of hemoglobin included in the supernatant obtained by centrifugating it with 1,000 g and the absorbance under the 414 nm of wavelength of the supernatant. In order to investigate relative level a comparative study of cytotoxicity, they measured the absorbance of supernatant with adding 1% triton X-100 (sigma, USA) to the human erythrocyte cell. Making the cytotoxicity of 1% triton X-100 to become a 100%, the present inventors calculated hemolysis of the peptides (experimental group 1 and 2) and maternal peptides (control group) of the present invention according to the following mathematical formula. The results are shown in the below Table 3.

TABLE 2

Antimicrobial activity of the antibiotic peptide on a Gram positive bacterium and Gram negative bacterium

MIC (μM)

| Peptide | Gram negative bacterium | | | | Gram positive bacterium | | | |
|---|---|---|---|---|---|---|---|---|
| | *Escherichia coli* | *Pseudomonas aeruginosa* | *Proteus vulgaris* | *Salmonella typhimurium* | *Staphylococcus aureus* | *Listeria monocytogenes* | *Staphylococcus epidermidis* | *Bacillus subtilis* |
| HPA3NT3 | 4 | 2 | 8 | 2 | 2 | 2 | 2-4 | 2 |
| NT3-F1AF8A | 16-32 | 2 | 4 | 2 | 4-8 | 2 | 16 | 4 |
| NT3-F1AF8A-A2 | 4 | 2 | 2-4 | 1-2 | 4 | 2 | 2-4 | 2 |

As a result, as shown in the Table 2, the NT3-F1AF8A-A2 peptide (experimental group 2) comprising the amino acid sequence of SEQ. ID. NO:3 has similar or more than 2 times of antimicrobial activity comparing to HPA3NT3 peptide (control group 1) comprising the amino acid sequence of SEQ. ID. NO:1, and the NT3-F1AF8A peptide (experimental group 2) comprising the amino acid sequence of SEQ. ID. NO:2 has similar or less of antimicrobial activity comparing to HPA3NT3 peptide (control group 1) comprising the amino acid sequence of SEQ. ID. NO:1. in some strains. However, the decreased level of antimicrobial activity on the control group of the experimental group 1 is very low.

hemolysis (%) = [Mathematical Formula 1]

$$\left(\frac{\text{absorbance } A - \text{absorbance } B}{\text{absorbance } C - \text{absorbance } B}\right) \times 100$$

In the mathematical formula, absorbance A means the absorbance of the peptide solution under the 414 nm of wavelength, absorbance B means the absorbance of PBS under the 414 nm of wavelength and absorbance C means the absorbance of 1% triton X-100 under the 414 nm of wavelength.

TABLE 3

Meauserement of hemolytic activity of the antibiotic peptide

| Peptide | % Hemolysis (Concentration of each peptide, μM) | | | | | | |
|---|---|---|---|---|---|---|---|
| | 200 | 100 | 50 | 25 | 12.5 | 6.25 | 3.13 |
| HPA3NT3 | 37.23 | 11.35 | 7.12 | 0 | 0 | 0 | 0 |
| NT3-F1AF8A | 0 | 0 | 0 | 0 | 0 | 0 | 0 |
| NT3-F1AF8A-A2 | 0 | 0 | 0 | 0 | 0 | 0 | 0 |

As a result, HPA3NT3 peptide (control group) comprising the amino acid sequence of SEQ. ID. NO:1, as shown in the Table 3, generated 37.23% of hemolytic activity at 200 μM, on the contrary, both NT3-F1AF8A-A2 peptide (experimental group 2) comprising the amino acid sequence of SEQ. ID. NO:3 and NT3-F1AF8A peptide comprising the amino acid sequence of SEQ. ID. NO:2 (experimental group 1) did generate no hemolytic activity.

Therefore, it is confirmed that the antibiotic peptide of the present invention has little cytotoxicity herein (Table 3).

Example 4

Confirmation of Cytotoxicity in the Normal Cell Line

In order to confirm the cytotoxicity in the normal cell line, which was prepared by the <experimental example 1>, the present inventors measured the cytotoxicity using HaCaT cell line (Dr. N E. Fusenig, Heidelberg, Germany) and NIH3T3 cell line (ATCC(CRL-1658™)).

Specifically, they inject HaCaT cell line and NIH3T3 cell line, which were cultured in DMEM badge including 10% FBS (Fetal Bovine Serum), into 96-well plate with $3 \times 10^3$ each and cultured them for 24 hours, after then, they treated the peptides prepared by the <experimental example> to the HaCaT cell line and NIH3T3 cell line according to the concentration respectively and reacted them in the 5% $CO_2$ incubator for 24 hours. After culturing, they put 20 ul of MTT (Thiazolyl Blue Tetrazolium Bromide) solution (5 mg/ml in PBS), into each well and reacted them four hours. And they removed supernatant and melted MTT crystal prepared by adding 200 ul of DMSO, and then they studied the result at 560 nm.

As a result, as shown in the drawing 1 and 2, HPA3NT3 peptide (control group) comprising the amino acid sequence of SEQ. ID. NO:1 in both two cell lines had high cytotoxicity, to the contrary, there is little cytotoxicity in NT3-F1AF8A-A2 peptide (experimental group 2) comprising the amino acid sequence of SEQ. ID. NO:3 and NT3-F1AF8A peptide (experimental group 1).

Therefore, it is confirmed that the antibiotic peptide of the present invention has little cytotoxicity (Drawing 1 and 2).

Several manufacturing methods containing the antibiotic peptide are as follows, but not always limited thereto.

Manufacturing Example 1

Tablets (Direct Pressurization)

After straining 5.0 mg of antibiotic peptide, the present inventors mixed 14.1 mg of lactose, 0.8 mg of crospovidone USNF and 0.1 mg of magnesium stearate and prepared with purification.

Manufacturing Example 2

Tablets (Wet Granulating)

After straining 5.0 mg of antibiotic peptide, the present inventors mixed 16.0 mg of lactose and 4.0 mg of starch. And then, the present inventors let 0.3 mg of polysorbate 80 be melted into pure water and added the mixed solution properly and made them particulate. The present inventors strained the particulate after drying, and mixed with 2.7 mg of colloidal silicone dioxide and magnesium stearate. Finally, they pressurized the particulate and prepared with purification.

Manufacturing Example 3

Powders and Capsules

After straining 5.0 mg of antibiotic peptide, the present inventors mixed together with 14.8 mg of lactose, 10.0 mg of polyvinyl pyrrolidone, 0.2 mg of magnesium stearate. And then, the present inventors filled the mixture into No. 5 gelatin capsule using a proper device.

Manufacturing Example 4

Injections

The present inventors prepared the injections containing 100 mg of antibiotic peptide together with 180 mg of mannitol, 26 mg of $Na_2HPO_4 12H_2O$ and 2974 mg of distilled water.

INDUSTRIAL APPLICABILITY

An antibiotic peptide of the present invention can be effectively used as an ingredient of pharmaceutical composition for antimicrobial purpose, food additives and cosmetics because it has prominent antimicrobial activity and no cytotoxicity.

The invention claimed is:

1. An antibiotic peptide comprising the amino acid sequence of SEQ ID NO: 1, wherein Phenylalanine, which is located at the first and the eighth position of the antibiotic peptide, is substituted with alanine and cytotoxicity is decreased.

2. The antibiotic peptide according to claim 1, wherein the antibiotic peptide consists of the amino acid sequence of SEQ ID NO: 2.

3. An antibiotic peptide comprising the amino acid sequence of SEQ ID NO: 2, wherein an Asparagine, which is located at the thirteenth position of the antibiotic peptide, is substituted with a positively charged amino acid.

4. The antibiotic peptide according to claim 3, wherein the antibiotic peptide comprises the amino acid sequence of SEQ ID NO: 3.

5. The antibiotic peptide according to claim 3, wherein the positively charged amino acid is selected from the group consisting of lysine, arginine, and histidine.

6. A method for the prevention or treatment of a pathogenic bacterial disease, containing the step of administering pharmaceutically effective dose of the antibiotic peptide of claim 1 to a subject.

7. A method for the prevention or treatment of a pathogenic bacterial disease, containing the step of administering pharmaceutically effective dose of the antibiotic peptide of claim 3 to a subject.

* * * * *

SEQUENCE LISTING

<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<223> OTHER INFORMATION: HPA3NT3 peptide

```
<400> SEQUENCE: 1

Phe Lys Arg Leu Lys Lys Leu Phe Lys Lys Ile Trp Asn Trp Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: NT3-F1AF8A peptide

<400> SEQUENCE: 2

Ala Lys Arg Leu Lys Lys Leu Ala Lys Lys Ile Trp Asn Trp Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: NT3-F1AF8A-A2 peptide

<400> SEQUENCE: 3

Ala Lys Arg Leu Lys Lys Leu Ala Lys Lys Ile Trp Lys Trp Lys
1               5                   10                  15
```